US008454937B2

(12) United States Patent
Claudio

(10) Patent No.: US 8,454,937 B2
(45) Date of Patent: Jun. 4, 2013

(54) METHOD AND COMPOSITION FOR THE SITE-SELECTIVE DELIVERY USING VIRUSES ENCAPSULATED IN MICROBUBBLES

(75) Inventor: Pier Paolo Claudio, Huntington, WV (US)

(73) Assignee: Temple University—Of The Commonwealth System of High Education, Philadelphia, PA (US)

( * ) Notice: Subject to any disclaimer, the term of this patent is extended or adjusted under 35 U.S.C. 154(b) by 1059 days.

(21) Appl. No.: 11/894,821

(22) Filed: Aug. 22, 2007

(65) Prior Publication Data

US 2008/0063604 A1   Mar. 13, 2008

Related U.S. Application Data

(60) Provisional application No. 60/843,895, filed on Sep. 12, 2006.

(51) Int. Cl.
| A01N 63/00 | (2006.01) |
| A01N 65/00 | (2009.01) |
| A61K 48/00 | (2006.01) |
| A61K 9/127 | (2006.01) |
| A61B 8/00 | (2006.01) |

(52) U.S. Cl.
USPC ......... 424/9.52; 424/93.2; 424/450; 424/93.1

(58) Field of Classification Search
None
See application file for complete search history.

(56) References Cited

U.S. PATENT DOCUMENTS

| 5,542,935 | A | 8/1996 | Unger et al. ............... 604/190 |
| 6,369,039 | B1 * | 4/2002 | Palasis et al. ............ 514/44 R |
| 6,416,740 | B1 | 7/2002 | Unger et al. ............. 424/9.52 |
| 6,743,779 | B1 | 6/2004 | Unger et al. ............. 514/44 |
| 2003/0078227 | A1 | 4/2003 | Greenleaf et al. ........ 514/44 |
| 2005/0283098 | A1 | 12/2005 | Conston et al. .......... 601/2 |

FOREIGN PATENT DOCUMENTS

WO    WO 97/33474    9/1997

OTHER PUBLICATIONS

Chen, et al. "Optimization of Ultrasound Parameters for Cardiac Gene Delivery of Adenoviral or Plasmid Deoxyribonucleic Acid by Ultrasound-Targeted Microbubble Destruction", Journal of the American College of Cardiology, 42(2): 301-308.*
Russell, et al. "Adenovirus Antigens—A Study of their Properties and Sequential Development in Infection", Journal of General Viriology, (1967) 1: 495-507.*
Ginsberg, et al. "Newer Aspects of Adenovirus Infections", American Journal of Public Health, (1959) 29(11): 1480-85.*
Wei, et al. "Basis for Detection of Stenosis Using Venous Administration of Microbubbles During Myocardial Contrast Echocardiography: Bolus or Continuous Infusion", Journal of the American College of Cardiology, (1998), 32: 252-60.*
Schutt, et al. "Injectable Microbubbles as Constrast Agents for Diagnostic Ultrasound Imaging: The Key Role of Perfluorochemicals", Angewandte Chemie, 42: 3218-35.*
R. Beeri, et al., "New Efficient Catheter-Based System for Myocardial Gene Delivery", Circulation, 2002, 106, 1756-59.
R. Bekeredjian, et al., "Ultrasound-Targeted Microbubble destruction Can Repeatedly Direct highly Specific Plasmid Expression to the Heart", Circulation, 2003, 108, 1022-26.
R. Bekeredjian, et al., "Use of Ultrasound Contrast Agents for Gene or Drug Delivery in Cardiovascular Medicine", Journal of the American College of Cardiology, 2005, 45(3), 329-35.
P.P. Claudio, et al., "Adenoviral RB2/p130 Gene Transfer Inhibits Smooth Muscle Cell Proliferation and Prevents Restenosis After Angioplasty", Circulation Research, 1999, 85, 1032-39.
P.A. Dijkmans, et al., "Microbubbles and ultrasound: from diagnosis to therapy", Eur. J. Echocardiography, 2004, 5, 245-56.
H. Hosseinkhani, et al., "Ultrasound Enhances the Transfection of Plasmid DNA by Non-viral Vectors", Curr. Pharm. Biotech., 2003, 4, 109-22.
C.M. Howard, et al., "Ultrasound Guided Site Specific Gene Delivery System Using Adenoviral Vectors and Commercial Ultrasound Contrast Agents", Journal of Cellular Physiology, 2006, 209, 412-21.
C.M. Howard, "The role of ultrasound contrast agents in gene therapy", Applied Radiol., 2004, 33(10), 126-135.
M.S. Hughes, et al., "Targeted ultrasonic contrast agents for molecular imaging and therapy: a brief review", Medica Mundi, 2003, 47(1), 66-73.
I. V. Larina, et al., "Enhancement of Drug Delivery in Tumors by Using Interaction of Nanoparticles with Ultrasound Radiation", Tech. Cancer Res Treat., 2005, 4(2), 217-26.
I. Lavon, et al., "Ultrasound and transdermal drug delivery", Drug Discovery Today, 2004, 9(15): 670-676.
A. Lawrie, et al., "Microbubble-enhanced ultrasound for vascular gene delivery", Gene Therapy, 2000, 7, 2023-27.
A. Lawrie, et al., "Ultrasound Enhances Reporter Gene Expression After Transfection of Vascular Cells in Vitro", Circulation, 1999, 99, 2617-20.
D.L. Miller, et al., "Ultrasonic Enhancement of Gene Transfection in Murine Melanoma Tumors", Ultrasound in Med. & Biol., 1999, 25(9), 1425-30.
C.M. Newman, et al., "Ultrasound Gene Therapy: On the Road from Concept to Reality", Echocardiography, 2001, 18(4), 339-47.
K.-y. Ng, et al., "Therapeutic Ultrasound: Its Application in Drug Delivery", Med. Res. Rev., 2002, 22(2), 204-23.
W.G. Pitt, et al., "Ultrasonic Drug Delivery—A General Review", Expert Opin. Drug Deliv., 2004, 1(1), 37-56.
T.R. Porter, "Diagnostic and Therapeutic Utilization of Microbubbles", Acta Cardiol. Sin., 2005, 21, 77-88.
M. Shimamura, et al., "Development of efficient plasmid DNA transfer into adult rat central nervous system using microbubble-enhanced ultrasound", Gene Therapy, 2004, 11, 1532-39.

(Continued)

Primary Examiner — Robert M Kelly
(74) Attorney, Agent, or Firm — Drinker Biddle & Reath LLP

(57) ABSTRACT

Methods and compositions for the site-selective delivery of a gene to a site within the body of an animal where virus not encapsulated within the microbubbles is inactivated, for example by treatment with a virus-inactivating agent.

47 Claims, No Drawings

OTHER PUBLICATIONS

R.V. Shohet, et al., "Echocardiographic Destruction of Albumin Microbubbles Directs Gene Delivery to the Myocardium", *Circulation*, 2000, 101, 2554-56.

J.M. Tsutsui, et al., "The use of microbubbles to target drug delivery", *Cardiovascular Ultrasound*, 2004, 2:23.

E.C. Unger, et al., "Gene Delivery Using Ultrasound Contrast Agents", *Echocardiography*, 2001, 18(4), 355-61.

E.C. Unger, et al., "Ultrasound Enhances Expression of Liposomal Transfection", *Invest. Radiol.*, 1997, 32(12): 723-727.

E. Unger, et al., "Microbubbles in molecular imaging and therapy", *Medica Mundi*, 2003, 47, 58-65.

S.D. Voss, et al., "Gene Therapy: A Primer for Radiologists", *RadioGraphics*, 1998, 18, 1343-72.

W. Wei, et al., "A novel approach to quantitative ultrasonic naked gene delivery and its non-invasive assessment", *Ultrasonics*, 2004, 43, 69-77.

\* cited by examiner

METHOD AND COMPOSITION FOR THE SITE-SELECTIVE DELIVERY USING VIRUSES ENCAPSULATED IN MICROBUBBLES

CROSS REFERENCE TO RELATED APPLICATION

This application claims the benefit of the filing date of U.S. Provisional Application Ser. No. 60/843,895, filed Sep. 12, 2006. The entire disclosure of which is incorporated herein by reference.

FIELD OF THE INVENTION

The invention relates to methods and compositions for achieving site-selective delivery of a virus within the body of an animal.

BACKGROUND OF THE INVENTION

Ultrasound is a diagnostic imaging technique. In using the ultrasound technique, sound is transmitted into a patient from a transducer. When the sound waves propagate through the body, they interact with tissues and fluids in the body and are partially or wholly reflected, or absorbed, depending on the acoustic properties of the tissues and fluids. Sound waves reflected from within the body can be detected by the receiver in the transducer and processed to form an image, the contrast of which depends on the different acoustic properties of the tissues and fluids within the body.

The principles underlying image formation in ultrasound have directed researchers to develop gaseous contrast agents. Changes in acoustic properties or acoustic impedance are most pronounced at interfaces of different substances with greatly differing density or acoustic impedance, particularly at the interface between solids, liquids and gases. When sound waves encounter such interfaces, the changes in acoustic impedance result in a more intense reflection of sound waves and a more intense signal in the ultrasound image. An additional factor affecting the efficiency or reflection of sound is the elasticity of the reflecting interface, with more elastic surfaces resulting in more efficient reflection of sound. Gas bubbles present highly elastic gas-liquid interfaces. To improve the quality of ultrasound images, researchers have been able to develop ultrasound contrast agents based on gas bubbles. The use of ultrasound contrast agents is discussed in the treatise *Ultrasound Contrast Agents: Basic Principles and Clinical Applications* by B. B. Goldberg, et al. (Eds.), Taylor & Francis (2nd Edition, 2001).

Another area of significant research effort is in the area of targeted drug delivery. One of the major challenges is achieving the systemic delivery of nucleic acids directly into a tissue, for example, for gene therapy. This requires developing a vehicle that is able to protect the nucleic acid from degradation, while delivering the gene of interest to the specific tissue and specific subcellular compartment.

Viruses are attractive delivery vectors for genetic material because of their ability to efficiently transfer genes with sustained expression. Recombinant adenoviruses are one of the most common gene transfer vectors utilized in human clinical trials, but systemic administration of this virus will also be met by host innate and adaptive antiviral immune responses which can limit and/or preclude repetitive regimens. See H. Jiang, et al. "Recombinant adenovirus vectors activate the alternative complement pathway, leading to the binding of human complement protein C3 independent of anti-ad antibodies", *Mol. Ther.*, 2004, 10(6), 1140-42.

The use of ultrasound contrast agents has been suggested as a means of delivering genetic material to tissues. See R. Bekeredjian, et al., "Ultrasound-targeted microbubble destruction can repeatedly direct highly specific plasmid expression to the heart", *Circulation*, 2003, 108(8): 1022-26; R. Bekeredjian, et al., "Use of ultrasound contrast agents for gene or drug delivery in cardiovascular medicine", *J. Am. Coll Cardiol.*, 2005, 45(3), 329-35; P. A. Dijkmans, et al., "Microbubbles and ultrasound: from diagnosis to therapy", *Eur. J. Echocardiogr.*, 2004, 5(4), 245-56; H. Hosseinkhani, et al., "Ultrasound enhances the transfection of plasmid DNA by non-viral vectors", *Curr. Pharm. Biotechnol.*, 2003, 4(2), 109-22; I. V. Larina, et al., "Enhancement of drug delivery in tumors by using interaction of nanoparticles with ultrasound radiation", *Technol. Cancer Res. Treat.*, 2005, 4(2), 217-26; I. Lavon, et al., "Ultrasound and transdermal drug delivery", *Drug Discov. Today*, 2004, 9(15), 670-76; A. Lawrie, et al., "Microbubble-enhanced ultrasound for vascular gene delivery", *Gene Ther.*, 2000, 7(23), 2023-27; A. Lawrie, et al., "Ultrasound enhances reporter gene expression after transfection of vascular cells in vitro", *Circulation*, 1999, 99(20), 2617-20; D. L. Miller, et al., "Ultrasonic enhancement of gene transfection in murine melanoma tumors", *Ultrasound Med. Biol.*, 1999, 25(9), 1425-30; C. M. Newman, et al., "Ultrasound gene therapy: on the road from concept to reality", *Echocardiography*, 2001, 18(4), 339-47; K. Y. Ng, et al., "Therapeutic ultrasound: its application in drug delivery", *Med. Res. Rev.*, 2002, 22(2), 204-23; M. Shimamura, et al., "Development of efficient plasmid DNA transfer into adult rat central nervous system using microbubble-enhanced ultrasound", *Gene Ther.*, 2004, 11(20), 1532-39, E. C. Unger, et al., "Gene delivery using ultrasound contrast agents", *Echocardiography*, 2001, 18(4), 355-61; E. C. Unger, et al., "Ultrasound enhances gene expression of liposomal transfection", *Invest. Radiol.*, 1997, 32(12), 723-27; S. D. Voss, et al., "Gene therapy: a primer for radiologists", *Radiographics*, 1998, 18(6), 1343-72; W. Wei, et al., "A novel approach to quantitative ultrasonic naked gene delivery and its non-invasive assessment", *Ultrasonics*, 2004, 43(2), 69-77.

The theory of such approaches is that genetic material can be loaded into the contrast agent bubbles and then released and incorporated into cells when the bubbles of the contrast agent are ruptured by exposure to ultrasound. Unfortunately, where delivery of viruses encapsulated in microbubbles has been attempted, the delivery has been observed as being non-selective. For example, in experiments where ultrasound-guided delivery of recombinant adenovirus containing β-galactosidase was achieved to the heart in rats, the livers of all animals that received the virus also showed extensive β-galactosidase activity. R. V. Shohet, et al., "Echocardiographic Destruction of Albumin Microbubbles Directs Gene Delivery to the Myocardium", *Circulation*, 2000, 101, 2254-56. Therefore, improved methods are needed to achieve site-selective delivery of viruses within the body of an animal.

SUMMARY OF THE INVENTION

According to the invention, site-selective delivery of viruses within the body of an animal may be achieved by encapsulating the virus within a microbubble and treating the resulting microbubble preparation with a virus-inactivating agent to inactivate unencapsulated virus prior to administration of the preparation. The inventor has found that the lack of specificity encountered in prior attempts to deliver genetic material by encapsulation of viruses in microbubble ultrasound contrast agents is due to the presence of free virus that remains associated with the contrast agent preparation. For example, viruses may be attached to the outside surface, but not encapsulated within, the contrast agent bubbles. Consequently, the delivery of the virus within the body of the animal is not site-selective because free viruses within the contrast agent are not directed to the desired site. The release of such free viruses is not controlled by the targeted rupturing of the contrast agent bubbles.

In one aspect of the invention, there is provided a method for preparing a composition for the site-selective delivery of a virus to a site within the body of an animal, the method comprising:
(1) providing a composition comprising a microbubble, wherein the microbubble comprises
   (a) a gas,
   (b) a shell surrounding the gas, and
   (c) a virus encapsulated within the microbubble; and
(2) treating the composition with a virus-inactivating agent to render virus not encapsulated in the microbubble inactive.

In some aspects of the invention, the composition is used for the site-selective delivery of a virus to a specific site within the body of an animal in a method further comprising:
(1) administering the composition to the animal; and
(2) directing ultrasound waves to the specific site within the body of the animal to release the virus from the microbubble.

In another aspect of the invention, there is provided a composition made by the method of the invention, including the compositions made by the particular and preferred embodiments thereof.

In a further aspect of the invention, there is provided a method for the site-selective delivery of a virus to a specific site within the body of an animal, the method comprising:
(1) administering to the animal a composition comprising a microbubble, wherein the microbubble comprises:
   (a) a gas,
   (b) a shell surrounding the gas, and
   (c) a virus encapsulated within the microbubble;
   wherein virus within the composition that is not encapsulated within a microbubble is inactive; and
(2) directing ultrasound waves to the specific site within the body of the animal to release the virus from the microbubble.

Particular and preferred embodiments of this aspect of the invention are those, wherein the gas, microbubble shell and virus correspond to those described herein.

DETAILED DESCRIPTION OF THE INVENTION

Definitions

A "microbubble" as used herein refers to a microsphere comprising a shell with an approximately spherical shape surrounding an internal void comprising a gas.

The microbubble "shell" referred to herein refers to a membrane surrounding the internal void of the microbubble.

The term "gas" as used herein denotes a substance of low toxicity which either is in the gasous phase at room temperature and normal atmospheric pressure or which can undergo a phase change to the gasous phase at a transition temperature of about 70° C. or lower.

The term "ultrasound" means high frequency sound, having a frequency greater than 10 kHz.

A "virus" as used herein refers to an acellular biological entity comprising a viral vector surrounded by a protein shell ("capsid") and which is capable of transducing a eukaryotic cell. A virus may or may not be enveloped.

"Transduce" as used herein refers to the transfer of a virus's nucleic acid into a cell. A cell into which viral nucleic acid has been transferred is called a "transduced cell."

A "vector" is a composition of matter which comprises an isolated nucleic acid and which can be used to deliver the isolated nucleic acid to the interior of a cell.

A "viral vector" as used herein refers to a nucleic acid, comprising at least the signal(s) for packaging, that is packaged into a capsid to form a viral nucleocapsid.

A virus that is "inactive" refers to a virus that, due to contact with a virus-inactivating agent, is not capable of transducing a cell, transferring its viral vector, and expressing a polynucleotide that is encoded by the viral vector.

As used herein, a "virus-inactivating agent" refers to any agent that prevents a virus from transducing a cell. The agent can be a single component agent or a combination of components. It encompasses molecular agents as well as energy agents, such as, but not limited to, ultraviolet irradiation.

An "encapsulated virus" refers herein to a virus that is contained within a microbubble. The virus may be contained entirely within the internal void of the microbubble shell, or may be partially contained in the void and partially embedded; or the virus is completely embedded in the microbubble shell. An encapsulated virus cannot escape the microbubble to infect cells in the body unless the microbubble is exposed to ultrasound or another energy source of sufficient energy to release the encapsulated virus from the microbubble. It is believed that ultrasound effects release of encapsulated virus by mediating microbubble destruction, as a result of the cavitation of microbubbles induced by ultrasound application.

The expression "virus not encapsulated within a microbubble" refers herein to virus that is present in a composition comprising microbubbles but not encapsulated within the microbubble. The expression encompasses virus that may be part of or connected to a microbubble in such a way that the virus is capable of infecting cells without exposing the microbubble to ultrasound, or an energy source other than the body itself. Without being limited by any theory, it is believed that a virus that is associated with the external surface of a microbubble is bound non-covalently to the external surface of a microbubble. It is, however, possible that a virus may be partially embedded in the microbubble shell and still be able to infect cells in the absence of microbubble destruction. As such, the invention is not limited to inactivation of viruses completely external to a microbubble.

As used herein, "complement" refers to the set of complement proteins found in blood serum that can inactivate viruses. The term encompasses the set of all of the serum complement proteins, as well as any subsets of serum complement proteins that have virus-inactivating activity.

As used herein, "therapeutic molecule" refers to an agent having, or intended to have, a beneficial effect on a patient.

The term "site-selective delivery" means delivery of a substance to a site within the body of an animal selected by an operator of a method, which delivery occurs to a greater extent than delivery to other, non-selected, sites within the body of the animal.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Recombinant polynucleotide" refers to a polynucleotide having sequences that are not naturally joined together. An amplified or assembled recombinant polynucleotide may be included in a suitable viral vector, which is incorporated into a virus and used to transduce a suitable host cell. A recombinant polynucleotide may serve a non-coding function (e.g., promoter, origin of replication, ribosome-binding site, etc.) as well.

An "expression cassette" as used herein refers to a polynucleotide sequence containing a coding sequence of interest operably linked to promoter and regulatory sequences necessary for expression (e.g., transcription and, for polypeptides, translation) of the coding sequence. An expression cassette may comprise more than one coding sequence of interest. A vector may comprise more than one expression cassette. The coding sequence may encode a polypeptide or a nucleic acid, such as an antisense molecule, a ribozyme, an siRNA or the like.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

An "siRNA" as used herein is an RNA molecule comprising nucleotides that is targeted to a gene or polynucleotide of interest based on sequence homology. As used herein, the term siRNA encompasses all forms of siRNA including, but not limited to (i) a double stranded RNA polynucleotide, (ii) a single stranded polynucleotide, and (iii) a polynucleotide of either (i) or (ii), wherein such a polynucleotide, has one, two, three, four or more nucleotide alterations or substitutions therein.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, "ribozyme" refers to an RNA molecule possessing the ability to specifically cleave other single-stranded RNA in a sequence-specific manner analogous to DNA restriction enzymes.

As used in the specification and the appended claims, the singular forms "a," "an" and "the" include plural referents unless the context clearly dictates otherwise.

Microbubble Composition

The composition and methods for forming microbubbles as ultrasound contrast agents are well established in the art. Therefore, the person skilled in the art knows the materials and methods to form the microbubbles used in the present invention. See, e.g., *Ultrasound Contrast Agents: Basic Principles and Clinical Applications* by B. B. Goldberg, et al. (Eds.), Taylor & Francis (2nd Edition, 2001) the entire disclosure of which are incorporated herein by reference. Examples of procedures for the preparation of microbubbles are described in: U.S. Pat. No. 4,446,442, U.S. Pat. No. 4,684,479, U.S. Pat. No. 4,718,433, U.S. Pat. No. 5,088,499, U.S. Pat. No. 5,123,414, U.S. Pat. No. 5,271,928, U.S. Pat. No. 5,413,774, U.S. Pat. No. 5,445,813, U.S. Pat. No. 5,556,610, U.S. Pat. No. 5,597,549, U.S. Pat. No. 5,686,060, U.S. Pat. No. 5,773,527, U.S. Pat. No. 5,798,091, U.S. Pat. No. 5,827,504, U.S. Pat. No. 6,217,850, U.S. Pat. No. 6,416,740, U.S. Pat. No. 6,443,898, and European Patent 0458745, the entire disclosures of which are incorporated herein by reference.

Microbubbles comprise a shell surrounding an internal void comprising a gas. Because of the surface energy involved in formation of the interface between the different phases, the microbubbles are expected to be approximately spherical in shape, as a result of minimization of the area of the interface. However, the geometrical shape of the microbubble is not essential to the invention, and is therefore not limiting.

Microbubbles typically have a diameter between about 0.5 and 300 µm, preferably no more than about 200, 100, or 50 µm, and for intravascular use, preferably not more than about 10, 8, 7, 6, or 5 µm (measured as average number weighted diameter of the microbubble composition). It is believed that the ideal microbubble diameter is about 4 µm. This is small enough to prevent entrapment within the pulmonary capillary bed (ranging from 5 to 8 µm in diameter), but big enough to entrap and protect viruses such as adenoviruses (Ad) from the environment.

The materials used to form the microbubbles should be biocompatible. Biocompatible materials are materials that are non-toxic to a patient in the amounts in which they are administered, and preferably are not disease-producing, and most preferably, are harmless.

The microbubble shell is a membrane surrounding the internal void of the microbubble. Microbubble shells typically range from about 10 to about 200 nm in thickness and help to prevent destruction and diffusion of the gas core.

The microbubble shell typically comprises a surfactant or a polymer. Surfactants suitable for use in microbubble preparation include any compound or composition that aids in the formation and maintenance of a microbubble by forming a layer at the interface between the gas and the medium, usually an aqueous medium, containing the microbubble. The surfactant may comprise a single compound or a combination of compounds. It will be appreciated by the person skilled in the art that a wide range of compounds capable of facilitating formation of the microbubbles can be used in the present invention. The optimum surfactant can be determined through empirical studies that do not require undue experimentation. One practicing the art of the present invention will choose a suitable surfactant based upon such properties as biocompatibility. The surfactant should also be compatible with active virus (i.e. not be virus-inactivating). Preferred surfactants include lipids, including phospholipids and fluorinated lipids. Lipids that may be used include fatty acids; lysolipids; phosphatidylcholines; including dioleoylphosphatidylcholine; dimyristoylphosphatidylcholine, dipentadecanoylphosphatidylcholine, dilauroylphosphatidylcholine, dioleoylphosphatidylcholine, dipalmitoylphosphatidylcholine, and distearoylphosphatidylcholine; phosphatidylethanolamines, including dioleoylphosphatidylethanolamine; phosphatidylserines; phosphatidylglycerol; phosphatidylinositols; sphingolipids; sphingomyelin; glycolipids; ganglioside GM1; ganglioside GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate; cholesterol hemisuccinate; tocopherol hemisuccinate, lipids with ether and ester-linked fatty acids, polymerized lipids, diacetyl phosphate, stearylamine, cardiolipin, phospholipids with short chain fatty acids of 6-8 carbons in length, synthetic phospholipids with asymmetric acyl chains, 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmiic acid; cholesteryl (4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine; palmitoylhomocysteine; and combinations thereof; lauryltrimethylammonium bromide, cetyltrimethylammonium bromide, myristyltrimethylammonium bromide, alkyldimethylbenzylammonium chloride, benzyldimethyldodecylammonium bromide, benzyldimethylhexadecylammonium bromide, benzyldimethyltetradecylammonium bromide, cetyldimethylethylammonium bromide, cetylpyridinium bromide; pentafluoro octadecyl iodide, perfluorooctylbromide, perfluorodecalin, perfluorododecalin, perfluorooctyliodide, perfluorotripropylamine, and perfluorotributylamine. Polymers useful in for use in the present invention include proteins, particularly albumin, particularly human serum albumin, and other biocompatible polymers, including polycyanoacrylate and poly(t-butyloxycarbonylmethyl)glutamate.

The nature of the microbubble shell determines the flexibility of the microbubble, the effect of ultrasound, and the binding properties to specific cell types. See P. Dayton, et al., "Acoustic radiation force in vivo: a mechanism to assist targeting of microbubbles", *Ultrasound Med. Biol.*, 1999, 25(8), 1195-1201; P. A. Dayton, et al., "Optical and acoustical dynamics of microbubble contrast agents inside neutrophils", *Biophys J.*, 2001, 80(3), 1547-56; J. R. Lindner, et al., "Noninvasive imaging of inflammation by ultrasound detection of phagocytosed microbubbles", *Circulation*, 2000, 102(5), 531-38; T. R. Porter, et al., "Differences in Myocardial Contrast Produced with Transient Response Imaging When Using Intravenous Microbubbles Containing Gases of Different Molecular Weight", *Echocardiography*, 1997, 14(5), 441-46, the entire disclosures of which are incorporated herein by reference.

Additional components may optionally be included in the microbubble shells to impart desired characterstics to microbubbles. The microbubble may comprise a ligand or targeting molecule included in or bound to the microbubble membrane, wherein the ligand or targeting molecule binds to a target surface or tissue. See, e.g. U.S. Pat. No. 6,245,318; U.S. Pat. No. 6,264,917; P. A. Dayton, et al., "Targeted imaging using ultrasound," *J. of Magn. Reson. Imaging*, 2002, 16(4), 362-77; S. H. Bloch, et al., "Targeted imaging using ultrasound contrast agents," *IEEE Engineering in Medicine and Biology Magazine*, 2004, 23(5), 18-29; A. Klibanov, et al., U.S. Pat. Appl. Pub. No. 2005/0260189, the entire disclosures of which are incorporated herein by reference. Microbubbles incorporating such targeting substances within their shell are included within the scope of the invention. Examples of such targeting molecules that may be included includes: antibodies and antibody fragments, cell adhesion molecules, their receptors, cytokines, growth factors, peptide hormones, peptide mimetics, and fragments thereof; non-peptide agonists/antagonists or non-bioactive binders of receptors for cell adhesion molecules, cytokines, growth factors and peptide hormones; oligonucleotides and modified oligonucleotides; protease substrates or inhibitors; small molecule ligands of biological receptors; inactivated proteases. Where the ligands or targeting molecules are biopolymers, and the methods and compositions of the invention are used in humans, the molecules are preferably human in origin to reduce the possibility of immunogenicity.

As used herein, the term "gas" denotes a substance of low toxicity which is either in the gasous phase at room temperature and normal atmospheric pressure or which can undergo a phase change to the gasous phase at a transition temperature of about 70° C. or lower. When referring to a "gas" it will be understood that, except where the context otherwise requires, the term encompases gaseous elements and compounds, and also mixtures of elements and/or compounds which together have the requisite properties, for example a mixture of the vapour of a liquid in a gas. In preferred embodiments, the gas has high molecular weight and low solubility in water, since this promotes microbubble persistence. With regard to molecular weight, for example, particular embodiments of the invention include those, wherein the gas has a relative molecular weight up to about 50, between about 50 and about 100, between 100 and about 150, between 150 and about 200, between about 200 and about 300. With regard to water solubility, particular embodiments of the invention include those, wherein the gas has a mole fraction solubility (at 20° C. and normal atmospheric pressure) of about $1\times10^{-3}$ or lower, preferably about $1\times10^{-4}$ or lower, and more preferably about $1\times10^{-5}$ or lower.

For gases that are liquid at room temperature, the transition temperature is particular to the compound, typically corresponding to the boiling point. In some preferred embodiments of the invention, a transition temperature of between about 20° C. about 37° C., or human body temperature, is preferred. In such embodiments, the microbubbles may be initially formed from gas that is in the liquid phase. This may result in microbubbles that are more stable than microbubbles formed from gas that is in the gas phase. In some embodiments of the invention, the gas changes from a liquid into a gaseous phase upon administration to the patient, from the ambient or room temperature. Alternatively, the transition may be caused by localized heating within the body of the patient, up to a limit of about 70° C., which may be achieved using focused high energy ultrasound. In other embodiments the gas is in the gaseous state prior to administration of the microbubbles to the patient.

Representative classes of gases for inclusion in the microbubble thus include common gases such as air; nitrogen; oxygen; carbon dioxide; hydrogen; inert gases such as helium, argon, xenon or krypton; sulphur fluorides, such as sulphur hexafluoride, disulphur decafluoride or trifluoromethylsulphur pentafluoride; selenium hexafluoride; optionally halogenated silanes such as methylsilane or dimethylsilane; low molecular weight hydrocarbons (e.g. containing up to 7 carbon atoms), for example alkanes such as methane, ethane, a propane, a butane or a pentane, cycloalkanes such as cyclopropane, cyclobutane or cyclopentane, alkenes such as ethylene, propene, propadiene or a butene, and alkynes such as acetylene or propyne; ethers such as dimethyl ether; ketones; esters; halogenated low molecular weight hydrocarbons (e.g. containing up to 7 carbon atoms); and mixtures thereof. Advantageously at least some of the halogen atoms in halogenated gases are fluorine atoms; as in, for example, bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethyl fluoride, 1,1-difluoroethane and perfluorocarbons. Other halogenated gases include methyl chloride, fluorinated (e.g. perfluorinated) ketones such as perfluoroacetone and fluorinated (e.g. perfluorinated) ethers, such as perfluorodiethyl ether, and thioethers, such as trifluoromethyl sulfide.

Specific examples of gases that may be used in the present invention include: air, allene, argon, bromochlorofluoromethane, bromochlorodifluoromethane, bromodifluoromethane, bromofluoromethane, 3-bromo-1-pentene, bromotrifluoromethane, 1,2-butadiene, 1,3-butadiene, 1-butene, 2-butene, 1-butyne, 2-butyne, carbon dioxide, carbonyl sulfide, 1-chloro-1,1-difluoroethane, 2-chloro-1,1-difluoroethane, 1-chloro-1,1,2,2-tetrafluoroethane, chlorocyclopentene, chlorodifluoromethane, chlorodifluoronitromethane, chloroethane, chlorofluoromethane, 2-chloro-1,1,1,4,4,4-hexafluorobutyne, 1-chloro-1,1,2,2,2-pentafluoroethane, 1-chloro-1,2,2,2-tetrafluoroethane, chlorotrifluoromethane, cyclobutane, cyclopropane, 1,1,1,2,2,3,4,5,5,5-decafluoropentane, dibromodifluoromethane, 1,2-dibromo-1,1,2,2-tetrafluoromethane, 1,1-dichlorodiacetylene, 1,1-dichloro-2,2-difluoroethylene, 1,2-dichloro-1,2-difluoroethylene, dichlorodifluoromethane, 1,1-dichloroethane, 1,1-dichloroethylene, dichlorofluoromethane, 1,1-dichloro-1-fluoroethane, 1,1-dichloro-1,2,2,2-tetrafluoroethane, 2,2-dichloro-1,1,1-trifluoroethane, 1,1-difluoroethane, 1,2-difluoroethane, 1,2-difluoroethylene, difluoromethane, 2,2-difluoropropane, 1,1-dimethylcyclopropane, 1,2-dimethylcyclopropane, dimethylethylamine, 2,3-dimethyl-2-norbornane, 2,2-dimethylpropane, ethane, ethylcyclopropane, 3-ethyl-3-methyldiaziridine, ethyl vinyl ether, fluoroethane, 1-fluorobutane, helium, 1,1,1,2,3,3,3-heptafluoropropane, hexafluoro-1,3-butadiene, 1,1,1,2,3,3-hexafluoro-2,3-dichloropropane, 1,1,1,3,3,3-hexafluoropropane, hexafluoro-2-methyl-1-butene, 1,1,1,2,2,3-hexafluoropropane, hexafluoropropylene, iodotrifluoromethane, krypton, 3-methyl-1-butene, 2-methyl-1-butene-3-yne, 3-methyl-1-butyne, methylcyclobutane, methylcyclopropane, isopropylacetylene, methane, 2-methyl-1,3-butadiene, 2-methyl-butane, methyl ether, methyl isopropyl ether, methyl lactate, methyl nitrite, methyl sulfide, methyl vinyl ether, neon, nitrogen, nitrous oxide, 1-nonene-3-yne, octafluoro-2-butene, octafluorocyclobutane, octafluorocyclopentene, oxygen, 1,4-pentadiene, n-pentane, 1,1,1,3,3-pentafluorobutane, pentafluoroethane, 1,1,1,3,3-pentafluoropropane, 1-pentene, E-2-pentene, Z-2-pentene, perfluorobutane, perfluoro-1-butene, perfluoro-2-butene, perfluoro-2-butyne, perfluorocyclobutene, perfluorodimethylamine, perfluoroethane, perfluoromethane, perfluorohexane, perfluoropentane, perfluoro-1-pentene, perfluoropropane, perfluoropropylene, propane, propene, propyne, selenium hexafluoride, sulfur hexafluoride, tetrafluoroallene, 1,1,1,2-tetrafluoroethane, 1,1,2,2-tetrafluoroethane, tetrafluoromethane, trichlorofluoromethane, trifluoromethylsulfur pentafluoride, 1,1,2-trichloro-1,2,2-trifluoroethane, 1,1,1-trifluoroethane, trifluoromethane, vinyl acetylene, vinyl ether, and xenon, and mixtures thereof.

Preferred gases of the invention are fluorocarbon compounds, including: perfluorocarbons, including perfluoroalkanes; hydrofluorocarbons, including hydrofluoroalkanes; chlorofluorocarbons, including chlorofluoroalkanes; hydrochlorofluorocarbons, including hydrochlorofluoroalkanes; and halons (haloalkanes containing bromine, fluorine, and optionally chlorine). Perfluorocarbons, particularly perfluoroalkanes, are particularly preferred. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Also preferred is sulfur hexafluoride. The use of perfluorinated gases, for example perfluorocarbons such as perfluoropropane, perfluorobutanes, perfluoropentanes and perfluorohexanes and sulphur hexafluoride and may be particularly advantageous in view of the recognised high stability in the blood stream of microbubbles containing such gases. Other gases with physicochemical characteristics which cause them to form highly stable microbubbles in the blood stream may likewise be useful.

The gas preferably fills at least 50% of the void within the microbubble shell, in some embodiments filling at least 60%, at least 70%, at least 80%, or at least 90% of the void. In some embodiments, the gas substantially fills the void within the microbubble shell.

A variety of methods are known for the formation of microbubbles. The microbubbles may be prepared by forming a fine dispersion of the gas in an aqueous medium in the presence of the shell material in an aqueous medium. Sonication is preferred for the formation of microbubbles. Microbubbles may also be formed by applying a high-speed mixing technique, such as blending or milling/mixing, to a mixture of the gas, the shell material and the medium. Other techniques of forming microbubbles include gas injection (e.g. venturi gas injection), passage through a mechanical high shear valve (or double syringe needle) and two syringes, or an aspirator assembly on a syringe, or simple shaking. Microbubbles can also be generated by forming a supersaturated solution of gas in a surfactant solution by introducing the gas into the solution at elevated pressure.

When used to form the microbubbles, sonication of the medium comprising the gas and microbubble shell material can be accomplished in a number of ways. Sonication may be performed through an ultrasound transmitting septum or by penetrating a septum with an ultrasound probe such as an ultrasonicallyvibrating hypodermic needle. For example, a vial containing a surfactant solution and gas in the headspace of the vial can be sonicated through a thin membrane. The membrane can be made of materials such as rubber, Teflon, mylar, urethane, aluminized film, or any other sonically transparent synthetic or natural polymer film or film forming material. The sonication can be done by contacting or even depressing the membrane with an ultrasonic probe or with a focused ultrasound "beam." The ultrasonic probe can be disposable. In either event, the probe can be placed against or inserted through the membrane and into the liquid. Once the sonication is accomplished, the microbubble solution can be withdrawn from the vial and delivered to the patient. Sonication can also be performed within a syringe with a low power ultrasonically vibrated aspirating assembly on the syringe, similar to an inkjet printer. Also, a syringe or vial may be placed in and sonicated within a low power ultrasonic bath that focuses its energy at a point within the container. Larger volumes of microbubbles can be prepared by direct probe-type sonicator action on the aqueous medium in which microbubbles are formed in the presence of gas (or gas mixtures).

In addition to the surfactant, it may be desirable to incorporate other agents within the aqueous phase for the formation of microbubbles, or for formulating microbubbles for in vivo use. Such agents may advantageously include conventional viscosity modifiers, buffers such as phosphate buffers or other conventional biocompatible buffers or pH adjusting agents such as acids or bases, and osmotic agents (to provide isotonicity, hyperosmolarity, or hyposmolarity). Preferred solutions have a pH of about 7 and are isotonic. Examples of such agents include sodium chloride and sucrose.

Microbubble solutions may be stabilized, for example, by the addition of a wide variety of viscosity modifiers, including, but not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Glycerol, propylene glycol, polyethylene glycol, polyvinyl pyrrolidone, and polyvinyl alcohol may also be useful as stabilizers in the present invention.

Emulsifying and/or solubilizing agents may also be used, provided such agents do not inactivate encapsulated virus. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax.

Suspending and/or viscosity-increasing agents that may be used include, but are not limited to, acacia, agar, alginic acid, aluminum mono-stearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

In the carrying out the methods and formulations of the invention, it is most convenient to use microbubble compositions the suitability of which for in vivo use has been established in the art. Examples commercially available ultrasound contrast agents, ultrasound contrast agent compositions that have been used invesigationally. Examples of commercially available and investigational microbubbles are listed in Table 1.

TABLE 1

Commercially Available and Investigational Microbubbles.

| Name | Supplier | Description |
|---|---|---|
| AI-700 | Acusphere, Inc. | Porous microparticles created by spray drying a water-in-oil emulsion containing poly-d,l-lactide-co-glycolide, diarachidoylphosphatidylcholine, and ammonium bicarbonate and formulated into a dry powder drug product containing perfluorobutane excipients. The dry powder is reconstituted to give perfluorobutane microbubbles. |
| Definity ® | Bristol-Myers Squibb | Perfluoropropane microspheres are composed of perfluoropropane encapsulated in an outer lipid shell consisting of (R)-hexadecanoic acid, 1-[(phosphonoxy)methyl]-1,2-ethanediyl ester, monosodium salt; (R)-α-4-hydroxy-N,N,N-trimethyl-10-oxo-7-[(1-oxohexadecyl)oxy]-3,4,9-trioxa-4- |

TABLE 1-continued

Commercially Available and Investigational Microbubbles.

| Name | Supplier | Description |
|---|---|---|
| | | phosphapentacosan-1-aminium, 4-oxide, inner salt; and (R)-α-[6-hydroxy-6-oxido-9-[(1-oxohexadecyl)oxy]-5,7,11-trioxa-2-aza-6-phosphahexacos-1-yl]-ω-methoxypoly(ox-1,2-ethanediyl), monosodium salt (abbreviated MPEG5000 DPPE). |
| Imagent ® (Imavist ®) | Imcor Pharmaceuticals, Inc., San Diego, CA, USA | Reconstitutable microbubbles comprising dimyristoylphosphatidyl choline (9.2 mg), hydroxyethylstarch (75 mg) poloxamer 188 (polyethylene-polypropylene glycol copolymer composed of 2 hydrophilic polyoxyethylene chains connected by a hydrophobic polyoxypropylene chain) (2.1 mg), sodium chloride (75 mg) sodium phosphate buffer (36 mg) in a vial comprising 17% v/v perfluorohexane vapor in nitrogen and reconstituted with 10 ml sterile water. |
| Levovist ™ | Schering AG, Berlin, Germany | Reconstitutable granules consisting of 99.9% galactose and 0.1% palmitic acid reconstituted in sterile water to give microbubbles of air stabilized by the palmitic acid. |
| Optison ® | GE Healthcare | Microbubbles (mean diameter 3 to 4.5 μm) of perfluoropropane comprising human albumin (10 mg/mL), perfluoropropane (0.22 ± 0.11 mg/mL), and caprylic acid (0.12 mg/mL) in 0.9% aqueous sodium chloride at pH 6.4-7.4. |
| Quantison ™ | GE Healthcare | Microbubbles of air comprising human serum albumin |
| Sonavist ® | Schering | Air microbubbles that are approximately 1-2 μm in diameter with a biodegradable shell composed of polybutyl-2-cyanoacrylate |
| Sonazoid ® | GE Healthcare, Oslo, Norway | An aqueous suspension of perfluorobutane microbubbles coated with phospholipids obtained from hydrogenated egg phosphatidylserine. |
| SonoVue ® | Bracco, Princeton, NJ. USA | Reconstitutable lyophilised white powder comprising polyethylene glycol 4000 and distearoylphosphatidylcholine, dipalmitoylphosphatidylglycerol sodium (DPPG•Na), and palmitic acid as microbubble stabilizers, the head-space of the vial containing the sulphur hexafluoride gas. Reconstituted with 0.9% w/v aqueous sodium chloride to give sulfur hexafluoride microbubbles of average diameter 2-8 μm. |

The microbubbles may be prepared immediately prior to use. Alternatively, the microbubbles may be pre-prepared then lyophilized or spray-dried to provide a reconstitutable product. Examples of suitable processes for the preparation of reconstituable microbubbles are described in U.S. Pat. No. 5,686,060, U.S. Pat. No. 5,798,091, U.S. Pat. No. 6,217,850, U.S. Pat. Appl. Pub. No. 2006/0034770, WO94/01140, WO97/29783, the entire disclosures of which are incorporated herein by reference.

The microbubble compositions comprising virus may be prepared either by including the virus preparation during the initial formation of the microbubbles, or by reconstituting microbubbles in the presence of the virus. It is contemplated that, optionally, the virus-containing microbubbles may be lyophilized or spray dried to provide a reconstitutable virus-containing product.

Viruses and Viral Vectors

Viruses are an efficient method of delivering recombinant polynucleotides to mammalian cells. Generally, for use as gene delivery vectors, viruses are engineered to be unable to replicate. Elimination of the replication ability of a virus precludes the virus from autonomously replicating in infected cells and, therefore, the virus is non-pathogenic. Accordingly, genes needed for the replication phase of their life cycle (non-essential genes) are deleted from the viral genome, or rendered non-functional, and, optionally, replaced with an expression cassette encoding a molecule of interest. The viruses comprising the recombinant viral genome are produced by providing the non-essential genes in trans, either integrated into the genome of a packaging cell line or on an expression plasmid. Such a replication-defective, non-pathogenic virus is able to transduce the cell types it would normally infect, enabling expression of the expression cassette in the cells.

Viruses for delivery of recombinant polynucleotides to mammalian cells include adenoviruses, parvoviruses, such as adeno-associated viruses, retroviruses, such as lentiviruses (e.g. HIV), herpesviruses, such as herpes simplex virus, poxviruses, vaccinia viruses, baculoviruses and the like. See, for instance, U.S. Pat. Nos. 5,350,674 and 5,585,362, Miller and Rosman, *BioTechniques* 1992, 7, 980-90; Anderson, et al., *Nature,* 1998, 392, 25-30 Suppl.; Verma and Somia, *Nature,* 1997, 389, 239-42; Wilson, *New Engl. J. Med.,* 1996, 334, 1185-1187; Chen, et al., *Proc. Natl. Acad. Sci. USA,* 1997, 94, 1645-50; and Walther, et al., *Drugs,* 2000, 60(2), 249-71, the entire disclosures of which are incorporated herein by reference.

Standard techniques are used for synthesis and recombinant manipulation and preparation of viral vectors for use in the present invention, as well as the preparation of viruses containing the vectors. The techniques are generally performed according to conventional methods in the art and various general references, including *Molecular Cloning: A Laboratory Manual, Cold Spring Harbor Laboratory Press* by Sambrook, et al., Cold Spring Harbor, N.Y. (2001), *Current Protocols in Molecular Biology* by Ausubel, et al. (Rds.), John Wiley & Sons, New York (2005), and *Methods for General and Molecular Bacteriology* by Gerhardt et al. (Eds.) American Society for Microbiology, Washington, D.C. (1994), the entire disclosures of which are incorporated herein by reference.

According to an embodiment of the invention, a virus comprises a recombinant viral vector that comprises an expression cassette encoding a molecule of interest. The promoter, operatively linked to the coding sequence of the expression cassette and controlling expression of the molecule of interest, may be constitutive, inducible or tissue-specific. Expression of the molecule of interest may be transient or sustained in a transduced cell. The expression cassette may encode a polypeptide or a nucleic acid as a molecule of interest. Accordingly, expression of a molecule of interest encompasses transcription and translation of sequences encoding polypeptides, as well as transcription alone of sequences encoding nucleic acid molecules.

In one embodiment, expression of the encoded molecule of interest provides a therapeutic molecule to the transduced cell. The therapeutic molecule may be any therapeutic molecule that can be encoded in a polynucleotide or whose production in vivo can be modulated by a molecule encoded in a polynucleotide. Non-limiting examples of types of therapeutic molecules that can be encoded in an expression cassette in the instant invention include, but are not limited to, polypeptide enzymes, cytokines, hormones, antibodies, such as intrabodies or scFvs, a suicide gene, such as HSV-TK, a molecule that inhibits vascularization, a molecule that increases vascularization, tumor suppressors, such as p53 and p21, pro-apoptotic molecules, such as TRAIL, transcription factors, receptors, ligands, immunogenic molecules, anti-proliferative molecules, agonists, antagonists, anti-inflammatory molecules, antibiotics, antidepressants, prodrugs, anti-hypertensives, ant-oxidants, and the like.

Nucleic acids useful as molecules of interest, and in particular, as therapeutic molecules, in the present invention include, by way of example and not limitation, antisense DNAs and/or RNAs, ribozymes and siRNA. Nucleic acids which are useful in the invention may include those that reduce the expression of an undesirable molecule in vivo. Undesirable molecules include those that mediate or are involved in disease processes, particularly where overexpression of the molecule, such as HER2, is associated with a disease or disorder, such as breast cancer and gastric cancer.

Ribozymes, antisense or siRNA nucleic acid molecules can be used to alter expression of particular molecules. Ribozymes and their use for inhibiting gene expression are also well known in the art (see, e.g., Cech, et al., *J. Biol. Chem.*, 1992, 267, 17479-82; Hampel, et al., *Biochemistry*, 1989, 28, 4929-33; Eckstein, et al., WO 92/07065; and Altman, et al., U.S. Pat. No. 5,168,053, the entire disclosures of which are incorporated herein by reference). Through the modification of nucleotide sequences encoding these RNAs, molecules can be engineered to recognize specific nucleotide sequences in an RNA molecule and cleave it. Cech, *J. Am. Med. Assn.*, 1988, 260, 3030, the entire disclosure of which is incorporated herein by reference.

There are two basic types of ribozymes, namely, tetrahymena-type (Hasselhoff, Nature 1988, 334, 585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. The use of antisense molecules in therapeutic and screening applications are well known in the art. See, e.g., Skorski, et al., *Proc. Natl. Acad. Sci. USA*, 1994, 91, 4504, *Antisense Therapeutics*, edited by Agrawal, Humana Press, Totowa, N.J. (1996), and Tamm, et al., *Lancet*, 2001, 358(9280), 489-97, the entire disclosures of which are incorporated herein by reference.

Small interfering RNAs (siRNA) initiate an in vivo process called RNA interference (RNAi). RNAi is a phenomenon in a diverse range of organisms and cell types in which the introduction of double-stranded RNA (dsRNA) causes degradation of the complementary mRNA. In the cell, long dsRNAs are cleaved into short 21-25 nucleotide siRNAs by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, e.g., U.S. Pat. No. 6,506,559; Fire et al., *Nature*, 1998, 391(19), 306-11; Timmons, et al., *Nature*, 1998, 395, 854; Montgomery, et al., *Trends Genet.*, 1998, 14(7), 255-58; *RNA Interference (RNAi) Nuts & Bolts of RNAi Technology*, edited by D R. Engelke, Ed., DNA Press (2003); *RNAi A Guide to Gene Silencing*, edited by G. J. Hannon, Cold Spring Harbor Laboratory Press (2003); and MacRae, et al., *Science*, 2006, 311, 195-98. Application of siRNA technology in mammalian cells has been demonstrated. See, e.g., WO 00/44895, DE 101 00 586.5, and U.S. Pat. Appl. Pub. Nos. 20060166920 and 20060166910. Accordingly, the design and use of molecules for ribozyme, antisense or siRNA applications is known in the art.

The art is replete with exemplary molecules, and diseases or disorders where a patient may benefit from the expression or inhibition of expression of such molecules. For instance, an assessment of expression changes in gene families in a variety of human cancers has been pursued U.S. Pat. Appl. Pub. No. 20060168670. In addition, tissue-specific expression levels have been mapped for thousands of genes through expression profiling. Alon et al., *Proc. Natl. Acad. Sci. USA*, 1999, 96:6745-50; Iyer, et al., *Science*, 1999, 283, 83-87; Khan et al., *Cancer Res.*, 1998, 58, 5009-13; Lee, et al., *Science*, 1999, 285, 1390-93; Wang, et al., Gene, 1999, 229, 101-08; and Whitney, et al., *Ann. Neurol.*, 1999, 46, 42. Thus, the skilled artisan is able to select molecules useful in the practice of the present invention without undue experimentation.

In another embodiment, the expression cassette in the viral vector encodes a marker or tag molecule. Non-limiting examples of markers or tags include green fluorescent protein (GFP) and related derivatives, luciferase, chloramphenicol transferase, β-glucuronidase and β-galactosidase. Such markers or tags are useful for identifying transduced cells, tracking transduced cells and applications, such as drug-screening assays.

Virus-Inactivating Agents

Any virus-inactivating agent is suitable in the practice of the instant invention, provided that exposure to the virus-inactivating agent is sufficient to inactivate non-encapsulated virus in a composition comprising a microbubble, but does not compromise the structural or functional integrity of the microbubble. For instance, virus-inactivating agents that modify, cleave or otherwise inactivate proteins may not be suitable for contacting microbubbles comprising protein in its membrane. In addition, it is necessary that the virus-inactivating agent inactivate unencapsulated virus selectively without inactivating all the encapsulated virus, although partial inactivation of some of the encapsulated virus may be tolerable, provided a sufficient portion of the encapsulated virus remains active to be delivered to the desired site within the body. The virus-inactivating agent is applied in an amount and for a period sufficient to inactivate unencapsulated virus selectively without inactivating all the encapsulated virus.

Table 2 provides a non-limiting list of virus-inactivating agents and examples of viruses against which the agents are effective. Non-limiting examples of virus-inactivating agents include: complement; β-propiolactone (BPL); inorganic aluminum salts, such as aluminum sulfate, that cause small particles, such as bacteria and viruses as well as inorganic particles, to destabilize and combine into larger aggregates (which can be removed mechanically); methylene blue; guanidine hydrochloride; copper or iron ions alone or in the presence of peroxide; tri(n-butyl)phosphate detergent combinations; infusions and extracts of grapes, wine and grape juice; caprylate; formaldehyde; hydrophobic photoinduced alkylating probe 1,5 iodonaphthylazide (INA); cationic beta-vinyl substituted meso-tetraphenylporphyrins; high-molecular-weight cellulose sulfate, dextran sulfate, and polystyrene; sulfonate; ethyleneimines; zerovalent iron; ultraviolet (UV) radiation (over 100 mJ/cm$^2$); infrared laser rays; photodynamic treatment (PDT) with visible light using methylene blue (MB), rose bengal (RB), uroporphyrin (UP) or aluminum phthalocynine tetrasulphonate (AlPcS4) as photosensitizers; monochloramine exposure; combination of ultraviolet (UV), free chlorine (Cl$_2$), and conversion to chloramines (for adenovirus, sequential addition of chlorine and conversion to chloramines is more effective than using preformed chloramines; UV disinfection (typical dose of 40 mJ/cm$^2$) followed by the sequential addition of chlorine to a solution containing ammonia results in chloramines that effectively achieve a 4-log adenovirus inactivation); chlorine dioxide; heat-inactivation via incubation at a minimum of 56° C. up to 70° C.; high hydrostatic pressure; psoralen (20 μg/mL) and ultraviolet-B (UVB); 312 nm irradiation; solution of 1% sodium hypochlorite, 2% glutaraldehyde, and 0.25% sodium dodecyl sulfate; sodium hydroxide and CIP-1000 (Steris Corporation, Mentor, Ohio) at concentrations greater than 0.09 M and 0.9%, respectively, at treatment times greater than 10 minutes; chemical treatment, such as any acid or basic pH treatment, hydrogen peroxide, pepsin, chloroform, and solvent/detergents; physical treatment, such as high pressure, UV, gamma rays, and supercritical state; specific antibody against the virus; amotosalen and long-wavelength UV light; cobalt chelate CTC-96; N-chlorotaurine; ortho-phthalaldehyde; glutaraldehyde; Microcyn® (Occulus Innovative Sciences, Petaluma, Calif.), a novel super-oxidized water product with neutral pH and disinfectant activity; chlorine dioxide; ozone; ultraviolet-C (UVC) irradiation; liposomal povidone-iodine (PVP-1), peracetic acid (PAA) and formaldehyde; Virkon® S (Farnam Co., Phoenix, Ariz., an oxidative disinfectant used against a variety of bacteria, spores, fungi, and viruses; 8-methoxypsoralen (8-MOP); phthalocyanine derivatives; anthraquinones (derived by hot glycerin extraction of a plant, such as *Rheum officinale, Aloe barbadensis, Rhamnus frangula, Rhamnus purshianus*, and *Cassia angustifolia*); tachyplesin I and related isopeptides (antimicrobial peptides isolated from the hemocytes of the horseshoe crab; *Tachypleus tridentatus* and *Limulus polyphemus*); Gigasept® (Schülke & Mayr, Sheffield, UK) a highly efficient chemical disinfectant on the basis of succine dialdehyde and formaldehyde; concanavalin A; p-chloromercuribenzoate; benzalkonium chloride (BZK); Triton X100; citric acid; and a solution of benzalkonium chloride, Triton X100, and citric acid (solution is commercially available as Resiguard F).

TABLE 2

Examples of Virus-inactivating Agents

| Agent | Exemplary Viruses Inactivate |
| --- | --- |
| Complement | Adenovirus, Retrovirus, Baculovirus, Vaccinia virus, Herpes virus |
| β-propiolactone (BPL) | HIV, poliovirus |
| Tri(n-butyl)phosphate detergent combinations | HIV, Hepatitis B |
| Infusions and extracts of different grapes. Agents responsible for this property reside in the skin of the grape. Therefore, also wine itself or grape juice. | Herpes simplex virus; Poliovirus |
| Caprylate | Enveloped viruses |
| Hydrophobic photoinduced alkylating probe 1,5 iodonaphthylazide (INA) | Retroviruses |
| Cationic beta-vinyl substituted meso-tetraphenylporphyrins | Herpes simplex virus I |
| High-molecular-weight cellulose sulfate, dextran sulfate, and polystyrene sulfonate. | HIV, human papilloma virus |
| Ethyleneimines | Parvovirus, Semliki Forest Virus |
| Photodynamic treatment (PDT) with visible light using phenothiazine dyes, such as methylene blue (MB), rose bengal (RB), uroporphyrin (UP) and aluminum phthalocynine tetrasulphonate (AlPcS4) as photosensitizers | HIV, parvovirus, hepatitis B, hepatitis C |
| Combination of ultraviolet (UV), free chlorine (Cl$_2$), and conversion to chloramines. Sequential addition of Cl$_2$ and conversion to chloramines are far more effective than the use of preformed chloramines at achieving adenovirus inactivation; UV disinfection at typical doses of 40 mJ/cm$^2$ followed by the sequential addition of chlorine to solution containing ammonia ultimately results in chloramines that effectively achieve a 4-log adenovirus inactivation. | Adenovirus |

TABLE 2-continued

Examples of Virus-inactivating Agents

| Agent | Exemplary Viruses Inactivate |
| --- | --- |
| Psoralen (20 µg/ml) and UVB (312 nm) | Herpes simplex virus I |
| Specific antibodies against the virus to be inactivated | Any virus for which a specific antibody that inhibits transduction is available |
| Amotosalen and long-wavelength ultraviolet light | Enveloped viruses; some non-enveloped viruses |
| Cobalt chelate CTC-96 | Herpes simplex virus, Adenovirus (type 5) |
| N-chlorotaurine | Adenovirus (type 5) |
| Ortho-phthalaldehyde | Adenovirus |
| Glutaraldehyde | Adenovirus |
| Phthalocyanine derivatives | Vaccinia virus |
| Anthraquinones (derived by a number of plant extracts; hot glycerin extracts prepared from *Rheum officinale*, *Aloe barbadensis*, *Rhamnus frangula*, *Rhamnus purshianus*, and *Cassia angustifolia*). | Herpes simplex virus I |
| Concanavalin A | Herpes simplex virus I |
| Solution of quaternary ammonium, detergent, and citric acid (e.g., benzalkonium chloride, Triton X100, and citric acid commercially available as Resiguard F which contains. Also benzalkonium chloride, Triton X100, and citric acid, singularly | Vaccinia virus, herpesvirus |

In a preferred embodiment, the virus-inactivating agent is complement. The complement system is a biochemical cascade of reactions of the immune system and involves over 30 proteins in vivo. The proteins include both soluble proteins in blood plasma, as well as membrane-bound proteins. The function of the complement system in vivo is to clear pathogens from an organism via a number of different processes.

For use in the present invention, the set of complement proteins present in blood sera is suitable and sufficient to achieve viral inactivation. Accordingly, serum may also be used as a virus-inactivating agent in the present invention. In an embodiment, serum obtained from the intended recipient for the composition of the invention is the virus inactivating agent in the method of the invention. This embodiment is advantageous for precluding immunogenicity problems that may be possible with non-autologous complement. This embodiment is also advantageous because it avoids the potential problem of transmission of infective diseases which may occur if a blood product from another individual is used. Complement may also be purified from a biological source, such as serum, comprising endogenous complement. Alternatively, a mixture of recombinant proteins, comprising the complement proteins present in serum, may be used. Recombinant expression of proteins and methods of protein purification are well known in the art. Complement is also widely commercially available.

Virus inactivating agents such as complement may occur naturally within the body of animals. However, when it is stated herein that the composition comprising the microbubbles is "treated" with virus inactivating agent in preparing a composition the site-selective delivery of a virus to a site within the body of an animal, a process performed outside the animal's body prior to administration of the composition to the animal is contemplated. The term "treating the composition with a virus-inactivating agent" therefore does not encompass exposure of the composition to virus inactivating agent within the body of the animal that might occur after the microbubble-encapsulated virus has been administered to the animal.

The complement useful in the instant invention is not species limited. Preferably, to reduce the possibility of immunogenicity problems with xeno proteins, the complement is from the sera of an organism of the same species as the recipient of the microbubbles. For instance, microbubbles to be administered to a human are preferably treated with human complement.

Armed with the instant disclosure and the teachings in the art, the skilled artisan is able to evaluate the viral inactivating capacity of any agent in combination with any virus of interest and any microbubble using routine screening methods without undue experimentation.

The virus-inactivating capacity of an agent for a particular virus can be evaluated in vitro by exposing the virus to the agent and testing the ability of the treated virus to transduce a cell, compared to a virus that is mock-treated with the agent. An agent that reduces or precludes viral transduction of a cell is identified as a virus-inactivating agent.

An agent identified as a virus-inactivating agent may then be evaluated for effectiveness in selectively inactivating unencapsulated virus as compared to encapsulated virus with a particular type of microbubble. Microbubbles containing encapsulated virus are formed either by generating the microbubbles or reconstituting preformed microbubbles in presence of the virus. The microbubbles with encapsulated virus are then treated with the virus-inactivating agent or mock-treated as a control. Following the treatment or mock treatment the microbubbles are mixed with cells in vitro and subjected to ultrasound waves. A control experiment (to evaluate the potential for non-site-selective virus delivery) may be performed where the treated or mock treated microbubbles are mixed with cells in vitro but not subjected to ultrasound waves. The transduction efficiency of the agent-treated and mock-treated microbubbles is evaluated, for instance, using in vitro cell cultures. With a combination of microbubble materials, virus and virus-inactivating agent that is effective for use in the methods and compositions of the invention, subjecting the virus-containing microbubbles that have been treated with the virus-inactivating agent leads to viral transduction, whereas without ultrasonication, the microbubbles treated with the virus-inactivating agent show transduction that is substantially reduced relative to that observed mock-treated cells, and, ideally, no detectable transduction.

Optional Components in the Microbubbles

Optionally, the microbubbles of the invention may further encapsulate one or more substances in addition to the viral vector. Non-limiting examples include therapeutic molecules or contrast agents. Contrast agents include, but are not limited to, paramagnetic gases, such as atmospheric air, which contains traces of oxygen 17, or paramagnetic ions such as $Mn^{2+}$, $Gd^{2+}$, and $Fe^{3+}$, as well as superparamagnetic particles (ferrites, iron oxides $Fe_3O_4$) and may thus be used as susceptibility contrast agents for magnetic resonance imaging (MRI), radioopaque metal ions, such as iodine, barium, bromine, or tungsten, for use as x-ray contrast agents, and gases from quadrupolar nuclei, which may have potential for use as magnetic resonance contrast agents.

Exemplary therapeutic molecules include, but are not limited to, antineoplastic agents, such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, arabinosyl, hydroxyurea, procarbazine, and dacarbazine; mitotic inhibitors such as etoposide and the vinca alkaloids; radiopharmaceuticals such as radioactive iodine and phosphorus products; hormones such as progestins, estrogens, antiestrogens, growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; anti-helmintics, antimalarials, and antituberculosis drugs; biologicals such as immune serums, antitoxins and antivenins; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as *Mycobacteria, Corynebacteria*), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); vitamins such as cyanocobalamin retinoic acid, retinoids and derivatives such as retinol palmitate, and α-tocopherol; peptides including enzymes such as manganese super oxide dismutase and alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; radioactive particles or ions such as strontium, iodide rhenium and yttrium; and prodrugs, such as those disclosed in U.S. Pat. No. 6,443,898, the disclosure of which is hereby incorporated herein by reference in its entirety.

Use of the Microbubbles for the Site-Selective Delivery of Virus

The microbubbles of the present invention may be used either in vivo, ex vivo or in vitro for targeted delivery of viruses comprising recombinant viral vectors encoding a molecule of interest. Advantageously, in in vivo applications, the administration of the microbubbles of the invention reduces or inhibits non-specific viral transduction. Without being bound by theory, it is believed that such non-specific viral transduction results from virus bound non-covalently to the exterior of the microbubble in such a way that, upon administration, the virus is able, in the absence of ultrasound rupturing, to dissociate from the microbubble and transduce cells. The microbubbles of the instant invention, contacted as described herein with a virus-inactivating agent, comprise substantially no active virus competent to transduce cells in the absence of ultrasound-induced rupture of the microbubble.

The microbubbles are destroyed in the sonification zone, releasing their contents. Cavitation also creates small shock waves that increase cell permeability by disruption of the endothelial barrier, enabling hematogenous delivery of the viruses. W. G. Pitt, et al., "Ultrasonic drug delivery—a general review", *Expert Opin. Drug Deliv.,* 2004, 1(1), 37-56. In addition, the microbubbles protect the virus from rapid degradation by the immune system. C. M. Howard, "The role of ultrasound contrast agents in gene therapy", *Applied Radiology,* 2004, suppl. 126-135; W. G. Pitt, et al., "Ultrasonic drug delivery—a general review", *Expert Opin. Drug Deliv.,* 2004, 1(1), 37-56. This is particularly important in cardiovascular as well as cancer gene therapy of inaccessible tumors. The use of microbubbles may also limit the amount of inflammatory response to the viruses and may allow repeated injections.

The gas-filled microspheres effectively lower the energy threshold for non-thermal cavitation. This allows diagnostic transducers operating within the energy levels permitted by the United States Food and Drug Administration to be used for site-selective delivery.

Ultrasound is high frequency sound, with a frequency of about 10 kHz or greater. Frequencies that are preferred for use in the present invention are those above the range of human hearing, in the frequency range from about 20 kHz to about 20 MHz. Particularly preferred are frequencies used in diagnostic sonography scanners, which are in the range from about 1 MHz to about 15 MHz. The frequency and intensity of ultrasound used is determined by the requirement to achieve selective microbubble destruction at the site of delivery. The requisite parameters for optimizing microbubble destruction have been studied, and are known to the person skilled in the art. See, e.g. K. W. Walker, et al., "Ultrasound-mediated destruction of contrast agents. Effect of ultrasound intensity, exposure, and frequency", *Invest. Radiol.,* 1997, 32(12), 728-34. In general, it is expected that ultrasound intensities in the range from about 700 kPa and 200 kPa peak negative pressure will be effective to destroy the microbubbles selectively at the site of delivery.

In an embodiment of the invention, microbubbles are used in an in vitro setting, such as a cell culture. In such an application, the microbubbles may be added to the cells in cultures. Sonic energy can then be applied to the culture media containing the cells and microbubbles, thereby releasing the virus and making it available to transduce the cells in the culture. Similarly, in ex vivo applications, microbubbles are added to cells, tissue or an organ removed from an organism and sonic energy is applied to rupture the microbubbles to release the virus comprising a viral vector. For instance, a tissue or organ may be perfused ex vivo with blood or fluid to which the microbubbles are added. Sonic energy is applied to rupture the microbubbles.

In another embodiment, microbubbles treated with virus-inactivating agent according to the present invention are employed in the controlled delivery of virus comprising a recombinant viral vector to a region of an animal, for example a patient. The ability to rupture the microbubbles at the peak resonant frequency using ultrasound permits the controlled delivery of virus to a target region of the body of the animal. The microbubbles are ruptured by directing ultrasound to the target region, to release the virus in the target region. The echogenicity of the microbubbles allows the monitoring of the microbubbles following administration to a patient to confirm the presence of microbubbles in the desired region.

Accordingly, methods of controlled delivery of virus to a region of an animal involve the steps of: (i) administering to the patient microbubbles comprising encapsulated virus and non-encapsulated virus, wherein the virus comprises a viral vector and, wherein non-encapsulated virus is inactivated; and (ii) rupturing the microbubbles using ultrasound to release the virus comprising a viral vector in the region. Optionally, the microbubbles are monitored using ultrasound to confirm the presence of the microbubbles in the target region prior to the rupturing step. Upon release, virus may bind to and transduce cells proximal to the region where the microbubbles were ruptured. Transduced cells may express the molecule of interest encoded by the recombinant viral vector.

The animal may be any type of animal, but is preferably a vertebrate, more preferably a mammal, and most preferably human. By "region of an animal", it is meant the whole animal, or a particular area or portion of the animal. For example, by using the method of the invention, therapeutic delivery may be effected to the animal's heart or a animal's vasculature (that is, venous or arterial systems). The invention is also particularly useful in delivering virus to the animal's left heart, a region not easily reached heretofore with therapeutic delivery. Transesophageal ultrasound may be used to deliver virus to the posterior heart. Therapeutics may also be easily delivered to the liver, spleen and kidney regions of an animal, as well as other regions, using the present methods.

A common feature of malignant diseases is vascularization of tumors, which enables tumor growth and possible metastasis. Accordingly, a therapeutic molecule of interest can be delivered to vascularized tumors using the present methods and compositions. Cancers that may be treated by the methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers including, for example, malignant melanoma, basal cell carcinoma, squamous cell carcinoma, Kaposi's sarcoma, moles dysplastic nevi, lipoma, angioma, dermatofibroma, keloids, and psoriasis;

breast cancers including, for example, ductal carcinoma, lobular carcinoma, inflammatory breast cancer, medullary carcinoma, mucinous (colloid) carcinoma, Paget's disease of the breast, tubular carcinoma, phylloides tumor, metaplastic carcinoma, sarcoma, microcapillary carcinoma and adenoid cystic carcinoma; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified diseases.

The route of administration of the microbubbles will vary depending on the intended use. As one skilled in the art would recognize, administration of gene delivery systems of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, intrathecally or intratumorly, using a variety of dosage forms. One preferred route of administration is intravascularly. For intravascular use, the gene delivery system is generally injected intravenously, but may be injected intra-arterially as well. The microbubbles of the invention may also be injected interstitially or into any body cavity.

The useful dosage to be administered and the mode of administration will vary depending upon the age, weight, and type of animal to be treated, and the particular application intended. Typically, dosage is initiated at lower levels and increased until the desired effect, for instance a therapeutic effect, is achieved. Single administrations and multiple administrations are envisioned. Advantageously, the inactivation of non-encapsulated virus may contribute to the reduction or elimination of an undesirable immunogenic response against the virus, which might otherwise preclude multiple administrations of the microbubbles comprising virus. Such an undesirable immune response has been a problem for adenovirus vectors in gene delivery applications.

Preferably, each individual microbubble is capable of releasing substantially all of the encapsulated virus upon the application of ultrasound. The phrase "substantially all" refers to at least about 80%, and preferably at least about 90%, and most preferably, about 100%. In certain preferred embodiments, substantially all of the encapsulated virus is immediately released from the microbubble upon rupture. Further, it will be understood by one skilled in the art, once armed with the present disclosure, that the frequency and duration of ultrasound applied can be varied to achieve a desired rate of release of the encapsulated virus.

In preferred embodiments, at least about 50%, preferably, at least about 75%, more preferably at least about 90% and most preferably, about 100% of the encapsulated virus and gas contents of the microbubbles remain with the microbubble, because of their impermeability, until they reach the part of the body of the animal to which site selective delivery is desired and ultrasound is applied.

Generally, the delivery compositions of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about pH 5 to about pH 7.4.

For storage prior to use, the microbubbles of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile. Most preferably, the microbubbles are stored in an isotonic saline solution, although, if desired, the saline solution may be a hypotonic saline solution (e.g., about 0.3 to about 0.5% NaCl). The solution also may be buffered, if desired, to provide a pH range of about pH 5 to about pH 7.4. Suitable buffers for use in the storage media include, but are not limited to, acetate, citrate, phosphate and bicarbonate.

Bacteriostatic agents may also be included with the microbubbles to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid. One or more antioxidants may further be included with the microbubbles to prevent oxidation of lipid. Suitable antioxidants include tocopherol, ascorbic acid and ascorbyl palmitate.

Using the microbubbles of the present invention, ultrasonic energy interacts with the gas, bursting the microbubbles and allowing a virus to be released and able to transduce a cell. When the sonic energy encounters the interface of the gas within the tissue or fluid medium, local conversion of sonic energy into thermal and kinetic energy is greatly enhanced. The virus is thereby released from the microbubbles. Although not intending to be bound by any particular theory of operation, it is believed that the thermal and kinetic energy created at the site of the cell enhances cellular uptake of the virus and optional other components.

The delivery of virus encapsulated in the microbubbles of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull, a surgical window may be necessary.

The preferred method of performing site-selective virus delivery with the microbubbles comprising encapsulated virus is to apply energy to the target site and in doing so, release the virus from the microbubbles. The most preferred energy source is ultrasound.

Kits

The invention also provides a kit useful in preparing a composition of microbubbles comprising encapsulated virus for site-selective delivery of the virus. The kit comprises a composition comprising a microbubble, wherein the microbubble comprises a gas and a shell surrounding the gas. The kit further comprises a virus-inactivating agent. The kit further comprises instructional material providing directions for encapsulating virus within the microbubbles and then treating the microbubbles with the virus-inactivating agent.

The "instructional material" may comprise a publication, a recording, a diagram, or any other medium of expression which can be used to communicate the usefulness of the kit. The instructional material of the kit of the invention may, for example, be affixed to a container which contains the composition or the virus-inactivating agent or be shipped together with a container which contains the composition or virus-inactivating agent. Alternatively, the instructional material may be delivered to the user separately from the container with the intention that the instructional material and the other kit components be used cooperatively by the recipient. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Particular and preferred embodiments of this aspect of the invention are those, wherein the microbubble shell and the gas are the microbubble shells and gases used in the particular and preferred embodiments of the methods and compositions of the invention as described herein. Microbubbles comprising a fluorocarbon gas, particularly a perfluoroalkane, and a shell comprising a phospholipid are particularly preferred. Particular and preferred embodiments of this aspect of the invention are also those, wherein the virus-inactivating agent is a particular or preferred embodiment of the virus-inactivating agent used in the methods, and in preparing the compositions, of the invention as described herein. Complement is a particularly preferred virus-inactivating agent.

Optionally, the kit further comprises a viral vector for preparing a recombinant viral vector comprising a molecule of interest and a cell line useful for preparing viruses containing the viral vector. In one aspect, the viral vector is useful for preparing a virus selected from the group consisting of adenoviruses, parvoviruses, retroviruses, herpesviruses, poxviruses, vaccinia viruses, and baculoviruses. In one embodiment, the virus is an adenovirus and the virus-inactivating agent is complement.

The practice of the invention is illustrated by the following non-limiting examples.

EXAMPLES

General

Cell Lines, Cell Culture and Adenoviral Production

The DU-145 (human prostate adenocarcinoma), H23 (human lung adenocarcinoma), DB-1 (human melanoma), and 293 (primary human embryonic kidney) cell lines were obtained from the American Type Culture Collection (ATCC, Rockville, Md.) and were grown at 37° C., in a 5% $CO_2$/95% atmosphere, in Dulbecco's modified Eagle's medium (Mediatech Inc., Herndon, Va.) supplemented with 10% fetal bovine serum (FBS) from Hyclone, Inc, (Logan, Utah). Ad-GFP, which expresses the green fluorescence protein (GFP) marker gene under the strong cytomegalovirus (CMV) constitutive promoter, was generated using the AdEasy system (Carlsbad, Calif.), amplified as described by P. P. Claudio, et al., "Adenoviral RB2/p130 gene transfer inhibits smooth muscle cell proliferation and prevents restenosis after angioplasty", Circ. Res., 1999, 85(11), 1032-1039., and purified with the BD Adeno-X virus purification kit (BD Biosciences, Mountain View, Calif.) following the manufacturers' directions. A viral titer of $1.2 \times 10^{12}$ plaque-forming units (pfu)/mL was determined with a plaque assay for the Ad-GFP viruses. Because the packaging cells express the GFP gene during infection, the Ad-GFP viruses produced contain some GFP incorporated into or bound to their capsids. Therefore, the viruses are fluorescent, and they may also be detected by anti-GFP antibodies.

Procedure for Subjecting Microbubbles to Ultrasound Waves In Vitro

For the in vitro experiments that follow, ultrasound exposure was achieved with a 2.5 MHz phased array and a PowerVision 7000 scanner (Toshiba America Medical Systems, Tustin, Calif.). The acoustic output of the transducer was measured in water at 1 cm depth using a 0.5 mm broadband acoustic hydrophone (Precision Acoustics Ltd, Dorchester, UK). This hydrophone has good sensitivity over the range 1 to 20 MHz. Equal number of cells were plated in 6 well dishes in triplicates and insonified at 535 or 207 kPa peak negative pressure (corresponding to the 0 and −5 dB output settings, respectively) for 1 min after administration of 100 µL of bubbles reconstituted with the viral vector. Experiments were repeated with the delivery vehicle incubated with human complement for 30 min at 37° C. to inactivate unenclosed Ad-GFP and with controls (contrast bubbles only, in one well per agent). After 24 hours transduction efficiency was demonstrated by fluorescent microscopy.

Commercially Available Microbubble Preparations

The commercially available microbubble preparations listed in Table 3 were used in the examples that follow:

TABLE 3

Commercially Available Microbubbles Used in the Examples.

| Name | Supplier | Description |
|---|---|---|
| Levovist ™ | Schering AG, Berlin, Germany | Reconstitutable granules consisting of 99.9% galactose and 0.1% palmitic acid reconstituted in sterile water to give microbubbles of air stabilized by the palmitic acid. |
| Imagent ® (Imavist ®) | Imcor Pharmaceuticals, Inc., San Diego, CA, USA | Reconstitutable microbubbles comprising dimyristoylphosphatidyl choline (9.2 mg), hydroxyethylstarch (75 mg) poloxamer 188 (polyethylene-polypropylene glycol copolymer composed of 2 hydrophilic polyoxyethylene chains connected by a hydrophobic polyoxypropylene chain) (2.1 mg), sodium chloride (75 mg) sodium phosphate buffer (36 mg) in a vial comprising 17% v/v perfluorohexane vapor in nitrogen and reconstituted with 10 ml sterile water. |
| Optison ® | GE Healthcare, Princeton, NJ. USA | Microbubbles (mean diameter 3 to 4.5 μm) of perfluoropropane comprising human albumin (10 mg/mL), perfluoropropane (0.22 ± 0.11 mg/mL), and caprylic acid (0.12 mg/mL) in 0.9% aqueous sodium chloride at pH 6.4-7.4. |
| Sonazoid ® | GE Healthcare, Oslo, Norway | An aqueous suspension of perfluorobutane microbubbles coated with phospholipids obtained from hydrogenated egg phosphatidylserine. |
| SonoVue ® | Bracco, Princeton, NJ. USA | Reconstitutable lyophilised white powder comprising polyethylene glycol 4000 and distearoylphosphatidylcholine, dipalmitoylphosphatidylglycerol sodium (DPPG•Na), and palmitic acid as microbubble stabilizers, the head-space of the vial containing the sulphur hexafluoride gas. Reconstituted with 0.9% w/v aqueous sodium chloride to give sulfur hexafluoride microbubbles of average diameter 2-8 μm. |

Example 1

Preparation of Stabilized Perfluorobutane Microbubble Dispersion

A stabilized perfluorobutane microbubble dispersion is prepared as described in U.S. Pat. No. 6,217,850, substantially as follows. Hydrogenated egg phosphatidylserine (500.4 mg) is added to 100 ml water containing 5.4% (w/w) of a mixture of propylene glycol and glycerol (3:10 w/w). The mixture is shaken and heated to 80° C. for five minutes, allowed to cool to room temperature, shaken again and left standing overnight prior to use.

A portion (50 ml) of the resulting solution is transferred to a round-bottomed flask with a conical neck. The flask is fitted with a glass jacket having a temperature control inlet and outlet connected to a water bath maintained at 25° C. A rotor stator mixing shaft is introduced into the solution and to avoid gas leakage the space between the neck wall and the mixing shaft is sealed with a specially designed metal plug fitted with a gas inlet/outlet connection for adjustment of gas content and pressure control. The gas outlet is connected to a vacuum pump and the solution is degassed for one minute. An atmosphere of perfluoro-n-butane gas is then applied through the gas inlet.

The solution is homogenised at 23000 rpm for 10 minutes, keeping the rotor stator mixing shaft such that the openings are slightly above the surface of the liquid. A white coloured creamy dispersion is obtained, which is transferred to a sealable container and flushed with perfluoro-n-butane. The dispersion is then transferred to a separating funnel and centrifuged at 12000 rpm for 30 minutes, yielding a creamy layer of bubbles at the top and a turbid infranatant. The infranatant is removed and replaced with water. The centrifugation is then repeated twice, but now at 12000 rpm for 15 minutes. After the last centrifugation, the supernatant is replaced by 10% (w/w) sucrose. 2 ml portions of the resulting dispersion are divided between 10 ml flat-bottomed vials specially designed for lyophilisation, and the vials are cooled to −47° C. and lyophilized for approximately 48 hours, giving a white fluffy solid substance. The vials are transferred to a vacuum chamber, and air is removed by a vacuum pump and replaced by perfluorobutane gas. Prior to use, water is added and the vials are gently hand-shaken for several seconds, giving microbubble dispersions of perfluorobutane.

Example 2

Preparation of Perfluorohexane Microbubbles

A perfluorohexane microbubble composition is prepared as described in U.S. Pat. No. 5,798,091, substantially as follows. One litre of an aqueous solution comprising dimyristoyl phosphatidylcholine (0.45% w/v), and poloxamer 188 (0.15% w/v) is added to a high shear mixer and cooled in an ice bath. A course suspension of 1,1,2-trichlorotrifluoroethane (3.0% v/v) is made in the solution and the suspension is emulsified in a microfluidizer at 10,000 psi and 5° C. The resulting emulsion is added to one litre of a solution containing m-HES hydroxyethylstarch (3.6% w/v), sodium chloride (3.0% w/v), dibasic sodium phosphate (2.6% w/v), and monobasic Sodium phosphate (0.39% w/v). The mixture is then spray dried. Aliquots of powder (250 mg) are weighed into 10 ml tubing vials, sparged with perfluorohexane-saturated nitrogen at 13° C. and sealed. The nitrogen is saturated with perfluorohexane by passing it through three perfluorohexane filled gas washing bottles immersed in a 13° C. water bath. The vials are reconstituted with 5 ml water after inserting an 18-gauge needle as a vent to relieve pressure as the water was injected.

Example 3

Demonstration that Various Ultrasound Contrast Agents do not Induce Auto-Fluoresecence In Vitro Cells from cell lines H23 (human lung adenocarcinoma); DU-145 (human prostate adenocarcinoma) and DB-1 (human melanoma) were separately plated on glass coverslips, which were placed into 60 mm dishes, and 100 μL of the following commercially available contrast agents were added to the culturing medium: Levovist™, Imagent®, Optison®, Sonazoid®, and SonoVue®. Ultrasound was applied for two minutes to each dish using a 2.5 MHz phased array and a PowerVision 7000 scanner (Toshiba America Medical Systems, Tustin, Calif.). The acoustic output of the transducer was measured in water at 1 cm depth using a 0.5 mm broadband acoustic hydrophone (Precision Acoustics Ltd, Dorchester, UK). For each cell line/contrast agent combination, both a high and low ultrasound intensity was used for ultrasonication. After 24 hours, the cells were fixed in 4% paraformaldehyde and observed under a fluorescence microscope. No fluorescence was observed following exposure of H23, DU-145, or DB-1 cells to ultrasound at about 650 or 300 kPa peak negative pressure using any of the contrast agents investigated.

Example 4

Demonstration of Adenovirus Inactivation by Complement In Vitro

Du-145 and H23 cells were plated on glass coverslips, which were placed into 60 mm dishes, and 10 μL of Ad-GFP ($1\times10^{12}$ pfu/mL) was used to transduce the cells. In another set of dishes, transduction was attempted using 100 μL of a solution of Ad-GFP which was incubated with 10 volumes of human complement for 30 minutes at 37° C. prior to attempting cell transduction. After 24 hours, transduction efficiency was evaluated using fluorescence microscopy. Fluorescence was observed in DU-145 cells and H23 cells transduced with 10 μL of Ad-GFP ($1\times10^{12}$ pfu/mL). In contrast, no fluorescence was observed in observed in DU-145 cells and H23 cells where transduction was attempted with 100 μL of a solution of Ad-GFP that had been incubated with 10 volumes of complement for 30 minutes at 37° C. Therefore, thirty minutes of incubation of the adenovirus with complement was demonstrated to be sufficient to inactivate the adenovirus.

Example 5

Preparation of a Composition Containing Microbubble-Encapsulated Virus and Inactivation of Unencapsulated Virus Using Complement The commercially available contrast agents: Levovist™, Imagent®, Optison®, Sonazoid®, and SonoVue®, were reconstituted in the presence or absence of 2 mL of $1.2\times10^{12}$ pfu of Ad-GFP viruses. To inactivate unencapsulated and free adenoviruses, 1 volume of microbubbles formed in the presence of Ad-GFP were incubated with 10 volumes of a solution containing 60 mg/mL of human complement (Sigma Aldrich, Saint Louis, Miss.; the complement serum is prepared from pooled human plasma and lyophilized from serum) for 30 minutes at 37° C. The microbubbles were then washed with 10 mL of phosphate buffered saline solution. The milky white suspension floating on the top of the phosphate buffered saline was then collected and used in the in vitro and in vivo experiments that follow.

Example 6

Demonstration that Complement Inactivates Adenoviruses Adsorbed on the Microbubbles' Surface In Vitro Imagents microbubbles were prepared in the presence or absence of Ad-GFP and a portion of each set of bubbles was then treated with human complement for 30 minutes at 37° C. Microbubbles were then collected and reacted with a rabbit anti-GFP polyclonal antibody for 10 minutes at room temperature and then with an anti rabbit-TRITC conjugated antibody for another 10 minutes at room temperature. Microbubbles were placed between a glass slide and cover slip for immunohistochemistry and were sealed with nail polish. A deconvolution fluorescence microscope (Olympus IX81, Melville, N.Y.) was used to document fluorescence on/of the microbubbles.

Under fluorescence microscopy, Ad-GFP microbubbles not treated with complement but reacted with rabbit anti-GFP and anti-rabbit TRITC appeared as a yellow color indicating that the anti-rabbit TRITC-conjugated antibody was reacting with the anti-GFP antibody on the bubble's surface. On the other hand, Ad-GFP microbubbles treated with complement to inactivate the adenovirus and reacted with rabbit anti-GFP and anti-rabbit TRITC appeared as a green color indicating that the anti-rabbit TRITC conjugated antibody was not reacting with the anti-GFP antibody on the bubble's surface. Therefore, the complement treatment of the Ad-GFP bubbles inactivated the adenoviruses present on the bubble's surface, leaving intact and viable the adenoviruses encapsulated by the microbubbles without destroying the integrity of the Imagent® bubble shell.

Example 7

Demonstration that Complement does not Inactivate Virus Encapsulated within the Microbubbles Ad-GFP virus-containing microbubbles, both untreated and complement-treated were prepared as described in Example 3 with each of the contrast agents: Levovist™, Imagent®, Optison®, Sonazoid®, and SonoVue®. DU-145 cells were plated on glass coverslips, which were placed into 60 mm dishes. The different microbubble preparations were added to the DU-145 cells in the different dishes. One minute after addition of the microbubbles, ultrasound was applied for two minutes to each dish using a 2.5 MHz phased array and a PowerVision 7000 scanner (Toshiba America Medical Systems, Tustin, Calif.). The acoustic output of the transducer was measured in water at 1 cm depth using a 0.5 mm broadband acoustic hydrophone (Precision Acoustics Ltd, Dorchester, UK) For each cell line/contrast agent combination, both a high and low ultrasound intensity (207 kPa or 535 kPa peak negative pressure respectively) was used for subjecting the microbubbles to ultrasound waves. After 24 hours, the cells were fixed in 4% paraformaldehyde and observed under a fluorescence microscope. In addition, microbubbles alone were used as a negative control.

While all five contrast agents gave positive results, Imagent® and Sonazoid® contrast agents gave the best results. With sonication at 207 kPa peak negative pressure the GFP adenovector enclosed in Imagent® bubbles and treated with complement to inactivate the unencapsulated viral particles was delivered to 93% of the cells as compared to Imagent® bubbles that were not treated with complement to inactivate unencapsulated viruses.

Similar results were obtained with Sonazoid®, where 56% of the cells were transduced. At the lower ultrasound intensity, the complement-treated Imagent® and Sonazoid® microbubbles also delivered the GFP viruses to the cells, albeit at lower efficiency (27% of the cells and 28% of the cells respectively as compared to using untreated microbubbles).

Example 9

Demonstration of Site-Selective Virus Delivery In Vivo Using Complement-Treated Microbubbles Twenty nude mice (female NU/NU-nuBR outbred, isolator-maintained mice, 4-5 weeks old, from Charles River Laboratories, Wilmington, Mass.) were implanted with the human melanoma cell line DB-1 as a xenograft model (injecting $2.5 \times 10^6$ DB-1 cells per flank). After 20 days, when the tumors reached a volume of approximately 50 mm3, mice were sedated with 0.0133 mL/g of a mixture of Xylazine hydrochloride (10 mg/kg; Gemini, Rugby Laboratory, Rockville Centre, N.Y.) and Ketamine hydrochloride (20 mg/kg; Ketaset, Aveco, Fort Dodge, Iowa) administered intraperitoneally. The mice were placed on a mat warmed with 37° C. circulating water for the entire procedure. A 27-gauge needle with a heparin lock was placed within a lateral tail vein for administration of contrast material. The nude mice received an injection of 100 μL of Imagent® with/without Ad-GFP through the tail vein. The mice were split into 2 control groups (one mouse receiving 100 μL of PBS and ultrasound, and another control mouse receiving both Imagent® and ultrasound) and 6 active groups of 3 mice each (all receiving Imagent® and Ad-GFP viruses and ultrasound, but with/without pretreatment with the inactivating agent) (see Table 4).

TABLE 4

Experimental Design for In vivo Experiments

| Group # 1 | Group # 2 | Group # 3 | Group # 4 | Group # 5 | Group # 6 | Group # 7 | Group # 8 |
|---|---|---|---|---|---|---|---|
| Imagent ® + Ad-GFP | Imagent ® + Ad-GFP | Imagent ® + Ad-GFP | Imagent ® + Ad-GFP | Imagent ® + Ad-GFP | Imagent ® + Ad-GFP | CTRL 1 | CTRL 2 |
| Complement treated | Untreated | Complement treated | Untreated | Complement treated | Untreated | PBS + ultrasound | Imagent + ultrasound |
| 657 kPa | 657 kPa | 506 kPa | 506 kPa | 304 kPa | 304 kPa | 657 kPa | 657 kPa |

Grayscale ultrasound imaging was performed with an Aplio scanner (Toshiba America Medical Systems, Tustin, Calif.) using a broad bandwidth (4-10 MHz) linear array operating at 4.0 MHz. On the Aplio scanner three different acoustic output settings (100%, 64% and 20%) were employed for 4 minutes of exposure. These output power settings correspond to peak negative pressures of 657 kPa, 506 kPa and 304 kPa (respectively determined as described above). Ultrasound images were recorded as digital clips. The mice were sacrificed 48 hours after completion of the experiments, by placing them in a $CO_2$ gas jar placed in a ventilated fume hood. The tumors, heart, lungs and liver were harvested. Tissues to be sectioned for fluorescence analysis were placed in OCT (Sakura Finetek USA, Inc., Torrance, Calif.), frozen in liquid nitrogen, and stored at –80° C. Tissues to be sectioned for immunohistochemical analysis were preserved in neutral buffered formalin at 4° C. prior to embedding in paraffin. Specimens underwent phase contrast light, fluorescent microscopy, and H&E staining as well as immunohistochemistry using a monoclonal antibody against GFP.

For GFP imaging, frozen specimens were sectioned 3-4 μm thick using a cryostat. The sections were mounted with Vectashield®, a mounting medium comprising 99% glycerol (Vector Laboratories, Burlingame, Calif., USA) and expression of GFP was examined under fluorescence microscopy (Olympus, Melville, N.Y.). Sections were also processed for hematoxylin and eosin (H&E) staining.

For immunohistochemical (IHC) analysis, formalin fixed and paraffin embedded specimens were sectioned 3-4 μm thick. Sections were deparaffinized, re-hydrated and then quenched in 3% $H_2O_2$ for 20 minutes. Sections were washed with PBS and blocked in PBS containing 1% BSA for 20 minutes at 37° C. Monoclonal anti-GFP (Invitrogen, Carlsbad, Calif.) 1:2,000 was incubated 1 hour at 37° C. and then washed three times in PBS. Sections were incubated with an avidin-biotin-peroxydase complex (Vectastain® ABC Elite kit, Vector Laboratories, Burlingame, Calif.) and then washed two more times in PBS. The immunoreactivity was determined using diaminobenzidine (DAB) as the final chromogen. Finally, sections were counterstained with Meyer's Hematoxylin, dehydrated through a sequence of increasing concentration alcoholic solutions, cleared in xylene and mounted with epoxydic medium. During the immunohistochemical assay, proof slides were coupled with negative control slides on which the primary antibody was omitted.

In vivo, systemic delivery of Ad-GFP microbubbles not treated with complement and injected in the tail vein of nude mice resulted in nonspecific targeting of the GFP transgene following 4 minutes of ultrasound application. In fact, not only the tumors but also non-targeted organs, such as the heart and lungs, were positive to 488 nm fluorescence light excitation.

On the other hand, in vivo, systemic delivery of Ad-GFP microbubbles pretreated with complement resulted in specific targeting of the GFP transgene. In this set of mice, tumors targeted by 304 kPa of ultrasound were positive to the GFP marker, whereas heart and lung harvested from the same mice were negative to the 488 nm fluorescence light excitation.

Immunohistochemical analysis using a monoclonal antibody against GFP was also performed and confirmed the selective targeting. Untreated Ad-GFP microbubbles resulted in non-targeted GFP expression, evidenced by DAB positive staining in all tested tissues. In contrast, complement treated Ad-GFP microbubbles resulted in specific GFP expression targeted solely to the tumor and not the other tested tissues. Negative control mice were treated with ultrasound contrast agents alone and ultrasound did not show any immunohistochemical staining.

Example 10

Preparation of a Composition Containing Microbubble-Encapsulated Virus and Inactivation of Unencapsulated Virus Using Fetal Bovine Serum The commercially available contrast agents: Levovist™, Imagent®, Optison®, Sonazoid®, and SonoVue®, were reconstituted in the presence or absence of 2 mL of $1.2 \times 10^{12}$ pfu of Ad-GFP viruses. To inactivate unenclosed and free adenoviruses, 1 volume of microbubbles formed in the presence of Ad-GFP were incubated with 10 volumes of a Fetal Bovine Serum (FBS) (Hyclone, Logan, Utah) for 30 minutes at 37° C. Microbubbles were then washed with 10 mL of phosphate buffered saline solution. The milky white suspension floating on the top of PBS was then collected and used in the in vitro and in vivo experiments.

Example 11

Demonstration of the Feasibility of Site-Selective Virus Delivery Using Serum-Treated Microbubbles The feasibility of site-selective virus delivery using serum-treated microbubbles was demonstrated by using composition containing microbubble-encapsulated virus with unencapsulated virus inactivated using fetal bovine serum, prepared as described in Example 9, in in vitro and in vivo experiments performed essentially as described in Examples 6-9. The serum-treated microbubbles gave comparable results to the complement-treated microbubbles.

All references cited herein are incorporated by reference. The present invention may be embodied in other specific forms without departing from the spirit or essential attributes thereof and, accordingly, reference should be made to the appended claims, rather than to the foregoing specification, as indication of the scope of the invention.

What is claimed is:

1. A method for preparing a composition for the site-selective delivery of a virus to a site within the body of an animal, the method comprising:
    (1) providing a composition comprising a microbubble, wherein the microbubble comprises
        (a) a gas,
        (b) a shell surrounding the gas, and
        (c) a virus encapsulated within the microbubble; and
    (2) treating the composition with a virus-inactivating agent to render virus not encapsulated in the microbubble inactive.

2. A method for the site-selective delivery of a virus to a specific site within the body of an animal, the method comprising:
    (1) providing a composition comprising a microbubble, wherein the microbubble comprises
        (a) a gas,
        (b) a shell surrounding the gas, and
        (c) a virus encapsulated within the microbubble;
    (2) treating the composition with a virus-inactivating agent to render virus not encapsulated in the microbubble inactive;
    (3) administering the composition to the animal; and
    (4) directing ultrasound waves to the specific site within the body of the animal to release the virus from the microbubble.

3. The method according to claim 1, wherein the average microbubble diameter is not more than about 10 μm.

4. The method according to claim 3, wherein the average microbubble diameter is not more than about 5 μM.

5. The method according to claim 1, wherein the microbubble shell comprises a phospholipid.

6. The method according to claim 5, wherein the phospholipid is selected from the group consisting of phosphatidylcholines, phosphatidylglycerols, and phosphatidylserines.

7. The method according to claim 6, wherein the phospholipid is dimyristoylphosphatidylcholine.

8. The method according to claim 1, wherein the microbubble shell comprises a protein.

9. The method according to claim 8, wherein the protein is albumin.

10. The method according to claim 1, wherein the gas comprises nitrogen.

11. The method according to claim 1, wherein the gas comprises at least one fluorocarbon.

12. The method according to claim 11, wherein the gas comprises at least one perfluoralkane.

13. The method according to claim 12, wherein the gas comprises a perfluoroalkane selected from the group consisting of perfluorobutane and perfluorohexane.

14. The method according to claim 1, wherein the virus comprises a viral vector comprising an expression cassette encoding a molecule of interest.

15. The method according to claim 14, wherein the molecule of interest is a therapeutic molecule.

16. The method according to claim 14, wherein the molecule of interest is selected from the group consisting of green fluorescent protein, luciferase, chloramphenicol transferase, β-glucuronidase, and β-galactosidase.

17. The method according to claim 1, wherein the virus is selected from the group consisting of adenoviruses, parvoviruses, retroviruses, herpesviruses, poxviruses, vaccinia viruses, and baculoviruses.

18. The method according to claim 17, wherein the virus is an adenovirus.

19. The method according to claim 1, wherein the virus-inactivating agent comprises a chemical composition.

20. The method according to claim 19, wherein the virus-inactivating agent is complement.

21. A composition for the site-selective delivery of a virus to a site within the body of an animal, the composition formed by a process comprising:
    (1) providing a composition comprising a microbubble, wherein the microbubble comprises
        (a) a gas,
        (b) a shell surrounding the gas, and
        (c) a virus encapsulated within the microbubble; and
    (2) treating the composition with a virus-inactivating agent to render virus not encapsulated in the microbubble inactive.

22. The composition according to claim 21, wherein the average microbubble diameter is not more than about 10 μm.

23. The composition according to claim 21, wherein the average microbubble diameter is not more than about 5 μm.

24. The composition according to claim 21, wherein the microbubble shell comprises a phospholipid.

25. The composition according to claim 24, wherein the phospholipid is selected from the group consisting of phosphatidylcholines, phosphatidylglycerols, and phosphatidylserines.

26. The composition according to claim 24, wherein the phospholipid is dimyristoylphosphatidylcholine.

27. The composition according to claim 21, wherein the microbubble shell comprises a protein.

28. The composition according to claim 27, wherein the protein is albumin.

29. The composition according to claim 21, wherein the gas comprises nitrogen.

30. The composition according to claim 21, wherein the gas comprises at least one fluorocarbon.

31. The composition according to claim 30, wherein the gas comprises at least one perfluoralkane.

32. The composition according to claim 31, wherein the gas comprises a perfluoroalkane selected from the group consisting of perfluorobutane and perfluorohexane.

33. The composition according to claim 21, wherein the virus comprises a viral vector comprising an expression cassette encoding a molecule of interest.

34. The composition according to claim 33, wherein the molecule of interest is a therapeutic molecule.

35. The composition according to claim 33, wherein the molecule of interest is selected from the group consisting of green fluorescent protein, luciferase, chloramphenicol transferase, β-glucuronidase, and β-galactosidase.

36. The composition according to claim 21, wherein the virus is selected from the group consisting of adenoviruses, parvoviruses, retroviruses, herpesviruses, poxviruses, vaccinia viruses, and baculoviruses.

37. The composition according to claim 36, wherein the virus is an adenovirus.

38. The composition according to claim 21, wherein the virus-inactivating agent comprises a chemical composition.

39. The composition according to claim 38, wherein the virus-inactivating agent is complement.

40. The composition according to claim 21, wherein the composition is in the form of an aqueous solution.

41. A composition for the site-selective delivery of a virus to a site within the body of an animal, the composition comprising a microbubble, wherein the microbubble comprises:

(a) a gas, (b) a shell surrounding the gas, and (c) a virus encapsulated within the microbubble; and (d) inactive virus that is not encapsulated within the microbubble.

42. A method for the site-selective delivery of a virus to a specific site within the body of an animal, the method comprising:

(1) administering to the animal a composition comprising a microbubble, wherein the microbubble comprises:

(a) a gas, (b) a shell surrounding the gas, and (c) a virus encapsulated within the microbubble; and (d) inactive virus that is not encapsulated within the microbubble; and (2) directing ultrasound waves to the specific site within the body of the animal to release the virus from the microbubble.

43. A kit for preparing a composition for the site-selective delivery of a virus to a site within the body of an animal, the kit comprising:

(1) in a first compartment, a composition comprising a microbubble, wherein the microbubble comprises (a) a gas, and (b) a shell surrounding the gas;

(2) in a second compartment, a virus-inactivating agent; and (3) instructional material comprising instructions for preparing a composition of microbubbles comprising encapsulated virus for site-selective delivery of the virus.

44. The method according to claim 15, wherein the therapeutic molecule is a nucleic acid.

45. The method according to claim 44, wherein the nucleic acid is selected from the group consisting of antisense RNA, antisense DNA, ribozymes, and siRNA.

46. The composition according to claim 34, wherein the therapeutic molecule is a nucleic acid.

47. The composition according to claim 46, wherein the nucleic acid is selected from the group consisting of antisense RNA, antisense DNA, ribozymes, and siRNA.

* * * * *